United States Patent
Kennedy et al.

(10) Patent No.: US 6,945,985 B2
(45) Date of Patent: Sep. 20, 2005

(54) METHOD FOR MAKING FAST ABSORBING SUTURES BY HYDROLYSIS

(75) Inventors: John Kennedy, Guilford, CT (US); Mark S. Roby, Killingworth, CT (US); Matthew E. Hain, Wayne, NJ (US)

(73) Assignee: Tyco Healthcare Group LP, Norwalk, CT (US)

( * ) Notice: Subject to any disclaimer, the term of this patent is extended or adjusted under 35 U.S.C. 154(b) by 202 days.

(21) Appl. No.: 10/309,683

(22) Filed: Dec. 4, 2002

(65) Prior Publication Data

US 2004/0111116 A1 Jun. 10, 2004

(51) Int. Cl.$^7$ ............................................. A61B 17/04
(52) U.S. Cl. ................................. 606/228; 606/230
(58) Field of Search ........................................ 606/230

(56) References Cited

U.S. PATENT DOCUMENTS

| | | | |
|---|---|---|---|
| 3,728,839 A | * | 4/1973 | Glick ........................... 53/425 |
| 3,815,315 A | * | 6/1974 | Glick ........................... 53/425 |
| 4,135,622 A | | 1/1979 | Glick |
| 4,496,466 A | | 1/1985 | Whitehurst et al. |
| 5,019,093 A | | 5/1991 | Kaplan et al. |
| 5,035,858 A | * | 7/1991 | Held et al. ..................... 422/21 |
| 5,059,213 A | | 10/1991 | Chesterfield et al. |
| 5,439,102 A | | 8/1995 | Brown et al. |
| 5,716,376 A | | 2/1998 | Roby et al. |
| 5,760,118 A | * | 6/1998 | Sinclair et al. ............. 524/306 |
| 5,876,421 A | * | 3/1999 | Torgerson et al. .......... 506/228 |
| 6,136,018 A | | 10/2000 | Roby et al. |
| 6,138,440 A | | 10/2000 | Gemma |
| 6,440,364 B1 | * | 8/2002 | Vera et al. ..................... 422/33 |

* cited by examiner

*Primary Examiner*—Gary Jackson

(57) ABSTRACT

A method for making a surgical article is provided which comprises exposing a bioabsorbable material, e.g., a copolymer derived from a major amount of glycolide and a minor amount of lactide, to a humid environment either prior to coating the material or prior to or following sterilization of the material for a time period and at a temperature sufficient to predegrade the resulting surgical article.

23 Claims, 3 Drawing Sheets

METHOD FOR MAKING FAST ABSORBING SUTURES BY HYDROLYSIS

BACKGROUND

1. Technical Field

The present disclosure relates generally to bioabsorbable sutures. More particularly, the present disclosure is directed to bioabsorbable sutures having relatively short degradation times and methods for making such sutures by controlled exposure of a suture derived from bioabsorbable materials to humidity at elevated temperatures.

2. Background of Related Art

Bioabsorbable surgical devices, e.g., sutures, such as those made from glycolide and/or lactide and related compounds are known. For example, DEXON sutures (Davis & Geck, Danbury, Conn.) are absorbable multifilament sutures made from glycolide homopolymer, VICRYL sutures (Ethicon, Inc., Sommerville, N.J.) are made from a copolymer of glycolide and lactide, and POLYSORB sutures (United States Surgical, Norwalk, Conn.) are also made from a copolymer of glycolide and lactide. These sutures generally retain at least about 20 percent of their original strength at three weeks after implantation, with the suture mass being essentially absorbed in the body within about 60 to 90 days post implantation. In certain applications, however, it is desirable to employ sutures which lose their strength and/or mass in shorter periods of time.

Attempts to modify the physical properties of bioabsorbable materials have included adding fillers, irradiating and exposing the materials to boiling, soaking or steam treatment. See, U.S. Pat. No. 4,496,466. However, U.S. Pat. No. 4,135,622 discloses that exposure of dry polyglycolic acid sutures to small amounts of moisture for very short periods of time is sufficient to cause serious deterioration in the package and in vivo strength of the sutures on long term standing, and therefore discloses that the sutures must be kept and packaged "bone dry".

It would be advantageous to provide a bioabsorbable surgical article, e.g., a bioabsorbable synthetic multifilament surgical article, which exhibits and maintains desired tensile properties, handling characteristics and strength retention for relatively short periods of time while maintaining adequate stability within a package to provide acceptable shelf-life.

SUMMARY

It has been discovered that an article derived from a bioabsorbable material can be subjected to predegradation by controlled hydrolysis to provide a fast absorbing surgical article with a desired strength loss and degradation pattern. In one embodiment, a surgical article derived from bioabsorbable materials is subjected to predegradation prior to coating the surgical article by exposing the article to humidity at elevated temperatures for a time period sufficient to modify the physical properties of the resulting surgical article.

In another embodiment, a surgical article derived from a bioabsorbable material is subjected to predegradation prior to or after the step of sterilization by exposing the surgical article to humidity at elevated temperatures for a time period sufficient to modify the physical properties of the resulting surgical article.

DESCRIPTION OF THE PREFERRED EMBODIMENTS

Figure 1:
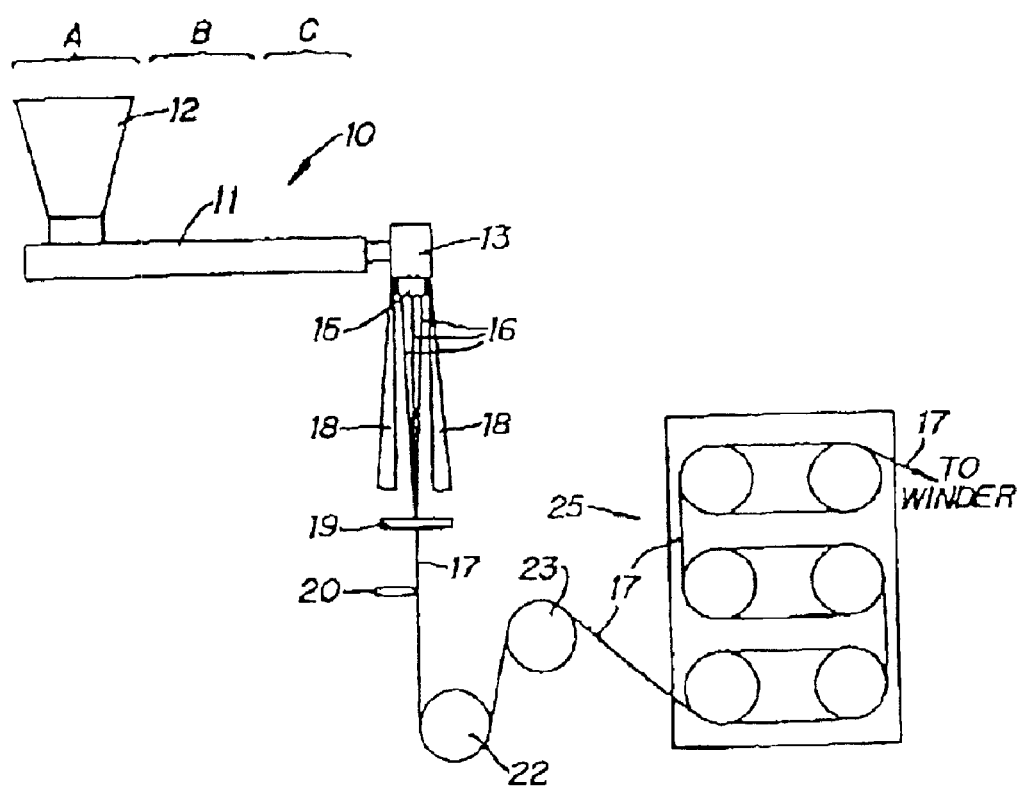
FIG. 1 is a schematic illustration of an apparatus which is suitable for manufacturing multifilament yarns in accordance with this disclosure.

Preferred embodiments of the present disclosure involve the use of bioabsorbable materials in the fabrication of surgical articles, e.g., sutures. It has been discovered that in forming the surgical articles, it is advantageous to predegrade the article either prior to or following sterilization of the article by exposing the article to a humidity at elevated temperatures for a time period sufficient to modify the physical properties of the resulting surgical article. It has also been discovered that in forming the surgical articles herein, it is particularly advantageous to predegrade the article prior to coating the article with a coating composition to provide better adherence of the coating when applied to the predegraded article.

Although the following discussion is presented in terms of multifilament surgical sutures, it should be understood that a wide variety of surgical articles can be processed using the method disclosed herein. These include but are not limited to monofilament sutures, clips and other fasteners, staples, sutures, pins, screws, prosthetic devices, wound dressings, drug delivery devices, meshes, woven and non-woven fabrics, and other implantable devices.

Generally, the starting material for forming the surgical articles are copolymers, block or random, derived from one or more monomers such as, for example, alkylene carbonates such as trimethylene carbonate, tetramethylene carbonate, dimethyl trimethylene carbonate and the like; lactones such as ε-caprolactone, dioxanones, dioxepanones and the like; absorbable cyclic amides; absorbable cyclic ether-esters derived from crown ethers; hydroxyacids capable of esterification such as both alpha hydroxy acid, e.g., glycolic acid and lactic acid, and beta hydroxyacids, e.g., beta hydroxybutyric acid and gamma hydroxyvaleric acid; polyalkyl ethers, e.g., polyethylene glycol and polyloropyline glycol, and combinations thereof. Preferred monomers for use herein to form the copolymers are glycolide, lactide, ε-caprolactone and trimethylene carbonate and combinations thereof. Most preferred are copolymers obtained by polymerizing a major amount of glycolide and a minor amount of lactide in the presence of a polyhydric alcohol initiator, e.g., glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)-ethylenediamine, N,N,N',N'-tetrakis(2-hydroxypropyl)ethylenediamine dipentaerythritol, allitol, dulcitol, glucitol, altritol, iditol, sorbitol, mannitol and the like. Copolymers made employing all of the various types of monomer addition, e.g., simultaneous, sequential, simultaneous followed by sequential, sequential followed by simultaneous, etc., are contemplated. However, it is preferred that the copolymers be formed as random copolymers.

In particularly useful embodiments, the copolymer used to form the surgical article contains from about 70 to about 98 and preferably from about 80 to about 95 weight percent glycolide derived units, the balance of the copolymer being derived from lactide. Most preferred is a random copolymer containing about 92 weight percent glycolide and about 8 weight percent lactide.

A process for manufacturing the surgical articles herein prior to exposing the surgical articles to a humid environment can include at least the operations of first melt extruding any of the foregoing copolymer resins at an extrusion temperature of from about 80° C. to about 250° C. by, for example, introducing pellets or powder of the resins to an extruder of a known and conventional type which is equipped with controls for regulating the temperature in various zones thereof, e.g., progressively higher temperatures in three consecutive zones such as zone 1 being maintained at a temperature of from about 80° C. to about 105° C., zone 2 being maintained at a temperature of from about 100° C. to about 105° C., and zone 3 being maintained at a temperature of from about 100° C. to about 110° C., to draw filaments from the copolymer resins. Next, the filaments can be subjected to braiding constructions known in the art. Illustrative of such braiding constructions and methods suitable for making multifilaments from the foregoing copolymers include those disclosed in U.S. Pat. Nos. 5,019,093; 5,059,213; and 6,136,018, the contents of which are incorporated by reference herein.

For example, FIG. 1 schematically illustrates a multifilament manufacturing operation suitable for use with the polymers described herein. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resin to be spun into filaments are introduced to the extruder through hopper 12. Any of the polymeric resins which are useful for the formation of fibers can be used herein. Motor-driven metering pump 13 delivers extruded resin at a constant rate through spinneret 15 possessing one or more orifices of desired diameter to provide a plurality of molten filaments 16. While spinneret 15 is shown schematically in FIG. 1 as extruding three filaments, it should be understood that the spinneret may extrude anywhere from 1 to 200 or more filaments simultaneously.

The filaments 16 travel downward and are gathered together by guide 19 to produce a yarn 17. The distance the filaments 16 travel after emerging from spinneret 15 to the point where they contact guide 19, i.e., the air gap, can vary and can advantageously be from about 0.5 m to about 10 m and preferably from about 1 m to about 2 m. A chimney 18, or shield, can be provided to isolate filaments 16 from contact by air currents which might otherwise affect the cooling or movement of the filaments in some unpredictable manner. In general, the temperature of zones A, B and C of the barrel 11 will vary depending on a number of factors such as the size of the powder or pellets and the rate of feed.

Once filaments 16 are gathered together by guide 19 to produce yarn 17, a spin finish can be applied to yarn 17, if desired, using any known technique. As shown in FIG. 1, the yarn may be wrapped around a lub godet 22 and one or more additional godets, for example, godet 23, to take up and adjust the tension on the yarn. The yarn 17 may then be passed to a heated draw frame 25. Draw frame 25 may be of any configuration. As shown in FIG. 1, draw frame 25 can include three pairs of godets which can be used to stretch the yarn or to allow relaxation and perhaps shrinkage of yarn 17. The speed at which the godets rotate and the temperature at which the draw frame is maintained will determine the amount of stretching and/or relaxation which occurs. Setting the various speeds and temperatures to achieve a desired result is within the purview of those skilled in the art.

Table I provides suitable ranges of values for spinning and stretching parameters useful in producing yarns from glycolide/lactide.

TABLE I

MELT SPINNING APPARATUS AND OPERATING CONDITIONS

| Apparatus Component, Operating Parameter | |
|---|---|
| Extruder barrel temp., zone A, degree C. | 200–250 |
| Extruder barrel temp., zone B, degree C. | 200–250 |
| Extruder barrel temp., zone C, degree C. | 200–250 |
| Extruder barrel pressure, psi | 700–2500 |
| Extruder barrel melt temp., degree C. | 200–250 |
| Pump size, cc per rev. | .16–.584 |
| Pump rpm | 10–50 |
| | for size .16 pump |
| | 3–11 |
| | size 584 pump |
| Pump temp., degree C. | 200–250 |
| Pump pressure, psi | 500–2500 |
| Pump melt temp., degree C. | 200–250 |
| Block temp., degree C. | 200–250 |
| Clamp temp., degree C. | 200–250 |
| Adapter temp., degree C. | 200–250 |
| Candle filter, screen, microns | 10–60 |
| No. of spinneret | 5–200 |
| Diameter of spinneret orifices, .001 in | 5–30 |
| Spinneret temp., degree C. | 200–250 |
| Spinneret pressure, psi | 500–2500 |
| Spinneret melt temp., degree C. | 200–250 |
| cc/hr output, per spinneret | 5–20 |
| First pair of godets, degree C. | 50–90 |
| First pair of godets, mpm | 80–275 |
| Second pair of godets, degree C. | 60–140 |
| Second pair of godets, mpm | 675–1610 |
| Draw (stretch) ratio | 2–6 |
| Third pair of godets, degree C. | ambient |
| Third pair of godets, mpm | 750–1400 |
| Shrinkage (relaxation), percent | 5–10 |

After drawing, the yarn may be sent to a winder where it can be placed onto spools for storage while awaiting further treatment and/or braiding. Any spin finish can be removed from the yarn by washing. The characteristics of the braided suture prepared in accordance with this disclosure, apart from the material of its construction, may include:

(1) overall suture denier;

(2) the pattern of the interlocking yarns expressed as the pick count, which is to say, the number of crossovers of individual sheath yarns per linear inch of suture;

(3) the number of sheath yarns comprising the braid;

(4) the denier of the individual filaments comprising each sheath yarn; and, (5) the denier of the core, where present.

(1) Overall Denier of the Suture

The overall denier of the braided suture can vary from about 25 to about 4300. Within this range, the ranges of overall denier for particular sutures are: from about 25 to about 80 denier; from above about 80 to about 150 denier; from above about 150 to about 300 denier; from above about 300 to about 600 denier; from above about 600 to about 950 denier; from above about 950 to about 1500 denier; from above about 1500 to about 2300 denier; and, from above about 2300 to about 4300 denier.

(2) Pattern of the Interlocking Sheath Yarns (Pick Count)

For a suture of any range of overall denier, pick count can vary from about 25 to about 100 crossovers/inch with about 40–85 crossovers/inch being preferred. For sutures constructed within any range of overall denier, as larger numbers of sheath yarns are employed, the pick-count for acceptable sutures will also increase within the above ranges.

For a suture of a particular range of denier and number of sheath yarns, pick count is advantageously established to achieve a balance in the properties desired. In general, with increasing pick count, surface roughness of the suture tends to increase and with decreasing pick count, the ability of the external braided sheath to contain the core (if present) tends to decrease even reaching the point where the braid may become so loose as to result in the core protruding therethrough. (3) The Number of Sheath Yarns The number of sheath yarns bears some relation to overall suture denier, the number generally increasing with the weight of the suture. Thus, across the range of suture weight (denier) indicated above, the braided suture of this invention can be constructed with from about 3 up to as many as about 36 individual sheath yarns constructed from individual filaments having the deniers discussed below.

Table II below sets forth broad and preferred ranges for the numbers of sheath yarns which are suitable for the construction of braided sutures of various ranges of overall denier. The pick counts of the sutures vary from about 50 to about 100 crossovers/inch and deniers of individual filaments vary from about 0.2 to about 6.0 for the broad range of number of sheath yarns and the pick counts vary from about 55 to about 80 and the deniers of individual filaments vary from about 0.8 to about 3.0, and advantageously from about 0.8 to about 1.6, for the preferred range of number of sheath yarns.

TABLE II

Sheath Yarns Related to Suture Denier

| Overall Suture Denier | Suture Size | Number of Sheath Yarns (Broad Range) | Number of Sheath Yarns (Preferred Range) |
|---|---|---|---|
| 25 to about 80 | 7/0, 8/0 | 3–12 | 3–8 |
| greater than about 80 to about 150 | 6/0 | 3–12 | 3–8 |
| greater than about 150 to about 300 | 5/0 | 4–16 | 6–14 |
| greater than about 300 to about 600 | 4/0 | 4–16 | 6–14 |
| greater than about 600 to about 950 | 3/0 | 4–16 | 6–14 |
| greater than about 950 to about 1500 | 2/0 | 6–24 | 12–20 |
| greater than about 1500 to about 2300 | 0 | 6–24 | 12–20 |
| greater than about 2300 to about 4300 | 1, 2 | 6–24 | 12–20 |

It is generally preferred that they be air entangled so as to minimize snagging during braid construction. Alternatively, the sheath yarns can be provided with a twist in lieu of being air entangled.

(4) Individual Filament Denier

The individual filaments comprising each sheath yarn can vary in size from about 0.2 to about 6.0 denier, preferably from about 0.8 to about 3.0 denier and more preferably from about 1.0 to about 1.8 denier. The number of such filaments present in a particular sheath yarn will depend on the overall denier of the suture as well as the number of sheath yarns utilized in the construction of the suture.

Table III sets forth some typical numbers of filaments per sheath yarn for both the broad and preferred ranges of filament denier:

TABLE III

Number of Filaments per Sheath Yarn

| approximate minimum | approximate maximum | Filament Denier |
|---|---|---|
| 45 | 450 | 0.2 |
| 15 | 150 | 0.5 |
| 5 | 50 | 1.5 |
| 3 | 40 | 1.8 |
| 1 | 15 | 6.0 |

(5) Core (Optional)

For all but the lowest range of overall denier, the braided suture herein can optionally be constructed around a filamentous core which itself can be braided or which can be provided in some other configuration such as a twist, ply, cable, etc. The filament(s) comprising the core need not be as fine as those comprising the sheath yarns. It is particularly advantageous for sutures of heavier to possess a core.

Table IV below provides some typical core deniers for sutures of various deniers.

TABLE IV

Core Denier Related to Suture Denier

| Overall Suture Denier | Suture Size | Denier of Optional Core (Broad Range) | Denier of Optional Core (Preferred Range) |
|---|---|---|---|
| from about 25 to about 80 | 8/0, 7/0 | none | none |
| greater than about 80 to about 150 | 6/0 | 0–80 | none |
| greater than about 150 to about 300 | 5/0 | 0–100 | none |
| greater than about 300 to about 600 | 4/0 | 0–125 | none |
| greater than about 600 to about 950 | 3/0 | 0–300 | 30–90 |
| greater than about 950 to about 1500 | 2/0 | 0–700 | 150–250 |
| greater than about 1500 to about 2300 | 0 | 0–1200 | 200–300 |
| greater than about 2300 to about 4300 | 1, 2 | 0–2400 | 250–650 |

Following the braiding constructions, braided filaments are then passed from a godet and stretched, e.g., with stretch ratios on the order of from about 2:1 to about 7:1 and preferably from about 3:1 to about 5:1, to effect its orientation and thereby increase its tensile strength. Stretching may be achieved by drawing the braided filaments at ambient temperatures or drawing the braided filaments while or after its has been heated.

In a stretching operation generally suitable for larger size sutures, e g, sizes 2 to 2/0, the braided filaments are drawn through a draw bath such as, for example, a hot glycerol or hot water (or other suitable liquid medium) draw bath, by means of a godet or any suitable arrangement of godets which rotate at a high speed to provide the desired stretch ratio. The temperature of the hot draw bath is advantageously from about 30° C. to about 60° and preferably is from about 40° to about 50°.

In an alternative stretching operation generally preferred for smaller suture sizes, e.g., sizes 3/0 to 8/0, the braided filaments are drawn by a godet or any suitable arrangement of godets through, e.g., a hot air convection oven chamber, at a temperature of from about 80° C. to about 150° C. and preferably from about 120° C. to about 140° C. to provide the desired amount of stretch. Following the stretching operation, the stretch filaments optionally may be subjected to an on-line annealing and/or additional stretching without shrinkage or relaxation with shrinkage operation as a result of which the filaments shrink.

In one embodiment of the present disclosure, the foregoing stretched braided filaments will be predegraded prior to coating the filaments, as discussed below, by subjecting the stretched braided filaments to hydrolysis. By predegrading the stretched braided filaments in this manner, the coating, when applied thereon, will better adhere to predegraded filaments. In general, the stretched braided filaments will be exposed to a humid environment for a time period and at a temperature sufficient to modify the physical properties of the resulting surgical article such as the control of the time of strength loss and degradation in vivo so that the element disintegrates and is bioabsorbed more quickly than the time that it would normally be completely absorbed without the predegradation treatment described herein. For example, the physical properties of the surgical article derived from a bioabsorbable material can be closely matched to the physiological requirements of the surgical procedure or repair. Thus, depending on the surgical need, a surgeon has available an element with a variable range of initial and in vivo physical properties.

In general, the stretched braided filaments will be placed in a humid environment, e.g., an environmental chamber, and exposed to a temperature of from about 80° F. to about 200° F. and preferably from about 125° F. to about 135° F. in a relative humidity of from about 20% to about 70% and preferably from about 45% to about 55%. The braided filaments should be exposed to the foregoing temperatures and relative humidities for a time period sufficient to degrade the article such that the physical properties, e.g., tensile strength, in vitro strength loss, can be modified according to the particular requirement of the surgical need or repair. Typically, a time period ranging from about 1 day to about 12 days, preferably from about 3 to about 10 days and most preferably from about 5 days to about 8 days is employed.

After the stretched braided filaments have been degraded to their particular degree, the predegraded filaments can then be coated to enhance the resulting surgical articles handling properties such as, for example, surgeon's throw, lubricity, knot run down and/or knot security. Suitable coating compositions include any commercially available coating known in the art. Preferred coating compositions for use herein are those disclosed in U.S. Pat. No. 5,716,376, the contents of which are incorporated by reference herein. Preferred coating compositions contain (a) a copolymer containing a major amount of ε-caprolactone and a minor amount of at least one other copolymerizable monomer and (b) a salt of a lactylate ester of a $C_{10}$ or greater fatty acid as the predominant component thereof.

Suitable caprolactone containing copolymers include copolymers which may be synthesized by well known conventional polymerization techniques; see, for example, Principles of polymerization, George Odian, III Edition; 1991, pp. 569–573, the contents of which are incorporated by reference herein.

Preferably, the caprolactone containing copolymer is obtained by polymerizing a major amount of epsilon-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

The copolymer for use in the coating composition herein can contain from about 70 to about 98 and preferably from about 80 to about 95 weight percent epsilon-caprolactone derived units, the balance of the copolymer being derived from the other copolymerizable monomer(s).

Suitable monomers which can be copolymerized with epsilon-caprolactone include alkylene carbonates which as trimethylene carbonate, tetramethylene carbonate, dimethyl trimethylene carbonate; dioxanones; dioxepanones; absorbable cyclic amides; absorbable cyclic ether-esters derived from crown ethers; hydroxyacids capable of esterification, including both alpha hydroxy acids such as glycolic acid and lactic acid and beta hydroxyacids such as beta hydroxybutyric acid and gamma hydroxyvaleric acid; olyalkyl ethers, e.g., polyethylene glycol and polyloropyline glycol, and combinations thereof; with glycolide being a preferred monomer.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis (2-hydroxyethyl)ethylenediamine, N,N,N',N'-tetrakis(2-hydroxypropyl)ethylenediamine dipentaerythritol, allitol, dulcitol, glucitol, altritol, iditol, sorbitol, mannitol, inositol, and the like; with mannitol being preferred.

The polyhydric alcohol initiator is generally employed in small amounts, e.g., from about 0.01 to about 5, and preferably from about 0.1 to about 3, weight percent of the total monomer mixture.

Suitable salts of a lactylate ester of a $C_{10}$ or greater fatty ester for use as the predominate component in the coating composition, i.e., in an amount greater than 50 weight percent, include, but are not limited to, magnesium stearoyl lactylate, aluminum stearoyl lactylate, barium stearoyl lactylate, zinc stearoyl lactylate, calcium palmityl lactylate, magnesium palmityl lactylate, aluminum palmityl lactlate, barium palmityl lactylate, zinc palmityl lactylate, calcium olelyl lactylate, magnesium olelyl lactylate, aluminum olelyl lactylate, barium olelyl lactylate, zinc olelyl lactylate, and mixtures thereof.

The bioabsorbable coating composition herein can be applied to the predegraded stretched braided filaments by any suitable process, e.g, passing the predegraded stretched braided filaments through a solution of the copolymer, e.g. in toluene, methylene chloride, etc., past a brush or other coating solution applicator, or past one or more spray nozzles dispensing the coating solution. The predegraded stretched braided filaments wetted with the coating solution is subsequently passed through or held in a drying oven for a time and a temperature sufficient to vaporize and drive off the solvent. If desired, the coating composition can optionally contain additional components, e.g., dyes, antibiotics, antiseptics, growth factors, anti-inflammatory agents, etc.

The amount of coating composition applied to the predegraded stretched braided filaments will vary depending upon the structure of the filaments, e.g., the number of filaments, tightness of braid or twist, the size of the filaments and its composition. Suitable coating levels range from about 0.3% to about 10% with about 0.5% to about 5% being preferred.

Figure 2:
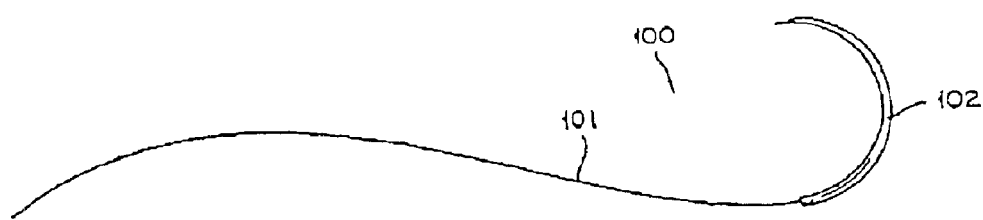
FIG. 2 is a perspective view of a suture made using the copolymers described herein attached to a needle; and, FIG. 3 is a graphical comparisons of the in vitro strength loss of a POLYSORB suture prepared in accordance with the scope of the present disclosure versus commercially available sutures.

As generally depicted in FIG. 2, the coated predegraded surgical article 101, e.g., a suture, can then be attached to a surgical needle 102 by methods well known in the art. Wounds may be sutured by passing the needled suture through tissue to create wound closure. The needle preferably is then removed from the suture and the suture tied. The coating advantageously enhances the surgeons's ability to pass the suture through tissue as well as to increase the ease and security with which he/she can tie the suture.

The attached predegraded article is then packaged by methods known in the art. Illustrative of such a package and method for forming the package are those disclosed in U.S. Pat. Nos. 4,135,622 and 6,138,440, the contents of which are incorporated by reference herein. For example, the attached article can be placed in a suture retainer package fabricated from, for example, a four layered water impervious laminate. The four layered water impervious laminate includes, for example, a first layer of heat sealable polyethylene, a second layer of aluminum foil, a third layer of polyethylene and a fourth layer of printable paper. The suture retainer package is conveniently formed by placing two pieces of the aforementioned laminate on top of each other with heat sealable polyethylene layers contacting each other. Three of the four edges are then sealed together using a standard heated die to form an envelope into which the attached suture is inserted. The fourth edge of the suture retainer package is sealed after the attached article is at least equilibrated and sterilized, which are discussed hereinbelow. Methods and materials for forming the four layered water impervious laminate can be any material known in the art for each of the layers.

After the article has been packaged, the packaged article can then be sterilized, if it has not already been, employing techniques well known in the art, e.g., by placing the packaged article in a sterilization chamber and exposing it to sterilization fluid such as, for example, ethylene oxide, for a time period sufficient to sterilize the article, e.g., about 1 to about 12 hours.

Following sterilization of the packaged surgical article, it is desirable to remove any remaining sterilization fluid and prevent any further degradation of the attached suture. Thus, to facilitate mass product it is desirable to equilibrate the moisture content of the sterilized article such as, for example, by placing the sterilized package in an environmental chamber having a controlled dew point of, e.g., about +10° C. to about −25° C., preferable from about 0° C. to about −20° C. and most preferably at about −10° C. to about −15° C. for about 96 to 336 hours. Such a moisture content in the atmosphere will typically result in a stabilized surgical article possessing an amount of moisture in the range of from about 0.3 to about 1.5 weight percent or more. The equilibrated sterilized package can then be sealed as discussed above, inserted in an envelope fabricated from a microbe-impervious material and hermetically sealed and stored for later use.

In accordance with a second embodiment of the method of the present disclosure, it is also contemplated that instead of predegrading the article prior to coating the stretched braided filaments as discussed above, the step of predegrading the surgical article herein can be carried out either prior to or following the step of sterilizing the packaged surgical article. It is preferred that the packaged surgical article be predegraded prior to sterilization. In general, the packaged surgical article can be predegraded in genarally the same manner and employing the same parameters as discussed above.

It is particularly advantageous that the surgical article herein be predegraded such that upon its use in a surgical procedure or repair the surgical article will possess about 50 percent of its original strength at day 5 and will have 0 percent strength after about 10–14 days. It is also advantageous that the surgical article will have a complete mass loss after a period of about 20 to about 60 days, preferably from about 35 to about 50 days and most preferably from about 40 to about 45 days.

It is further within the scope of the disclosure to incorporate one or more medico-surgically useful substances into the present articles, e.g., substances which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erthromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophase derived growth factor, alveolar derived growth factor, monocyte derived growth factor, magainin, and so forth. Some therapeutic indications are: glycerol and tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the suture in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with this disclosure are dyed by adding up to about a few percent and preferably about 0.2% dye, such as D&C Violet No. 2 to the resin prior to extrusion.

The following non-limiting examples are illustrative of the method of the present disclosure.

EXAMPLES 1–7

Needed unsterilized POLYSORB size 3/0 sutures were placed into unsealed packages of the type shown in U.S. Pat. No. 5,439,102. The unsealed packages were placed within an environmental chamber and exposed to a temperature of 130° F. and 50% relative humidity for a period of time ranging from 3 to 6 days as indicated in Table V. The sutures were then sterilized in ethylene oxide equilibrated at −14° C. dewpoint for 24 hours, the vacuum dried at 150° F. for 3 hours and 10 minutes and the packages sealed.

COMPARATIVE EXAMPLES

Figure 3:
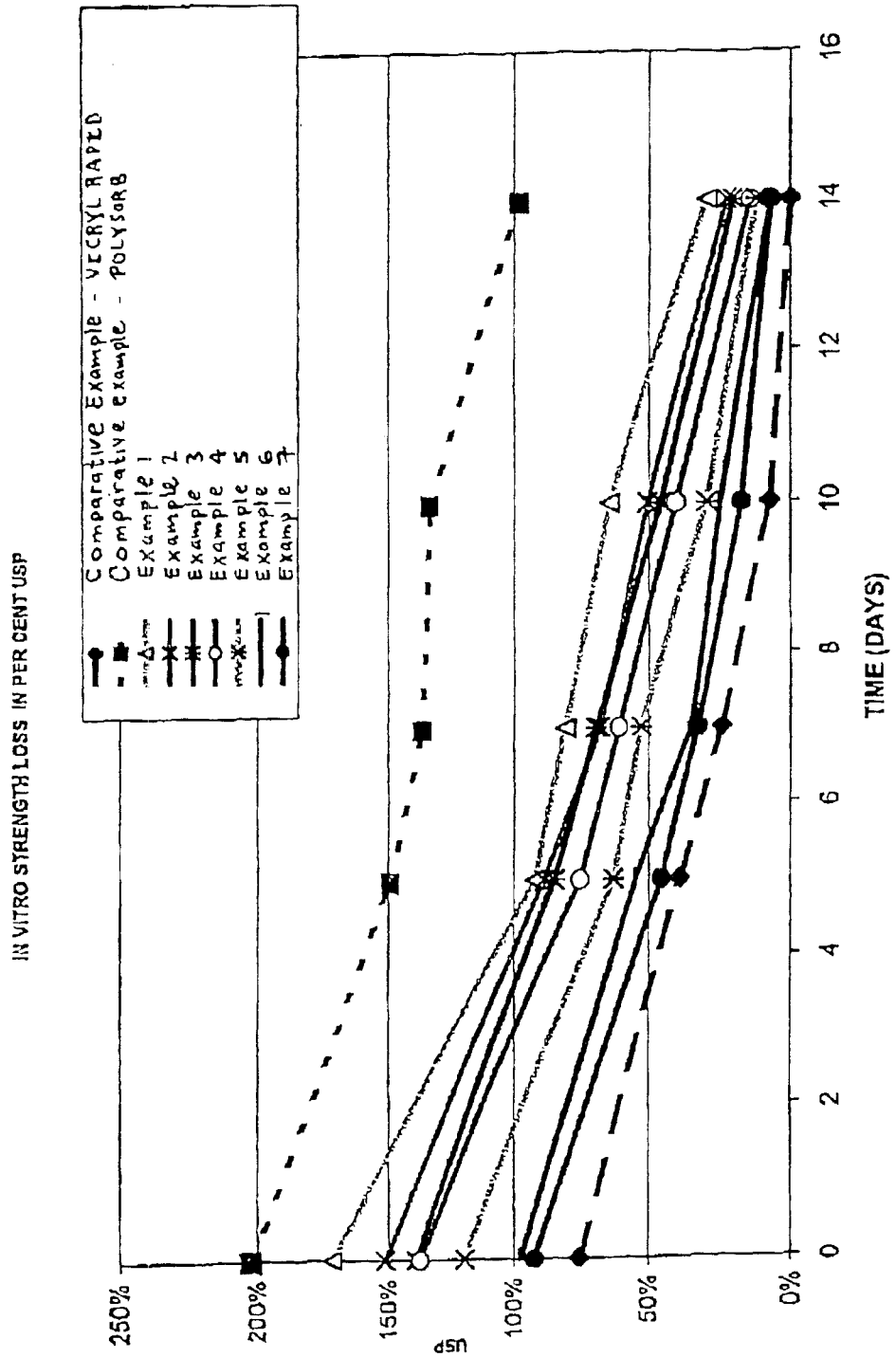

For comparison, the in vitro strength of POLYSORB size 3/0 sutures and VICRYL RAPID size 3/0 sutures (Ethicon, Inc., Sommerville, N.J.) were tested. Specifically, the sutures were placed in a petri dish in a solution of Sorenson's Buffer and the strength measured at intervals of 0 days, 5 days, 7 days, 10 days and 14 days as shown in Table V. The results were then plotted on a graph as illustrated in FIG. 3.

The in vitro strength retention of the sutures were tested as follows:

To simulate in vivo conditions, the suture samples were stored in a container filled with Sorenson's buffer solution at 50° C. After various periods of time, (i.e., 0 days, 5 days, 7 days, 10 days and 14 days) the suture samples were then removed from the container to test their knot-pull strength, using an Instron tensile tester. In vitro knot-pull strength retention is indicative of in vitro strength retention. The results of these tests are presented in Table V.

TABLE V

| Sample | Days of Exposure | Percent USP | | | | | Kilograms | | | | |
|---|---|---|---|---|---|---|---|---|---|---|---|
| | | 0 days | 5 days | 7 days | 10 days | 14 days | 0 days | 5 days | 7 days | 10 days | 14 days |
| VICRYL RAPID | 0 | 76% | 39% | 24% | 7% | 0% | | | | | |
| POLYSORB | 0 | 202% | 149% | 136% | 133% | 98% | 3.581 | 2.643 | 2.415 | 2.362 | 1.736 |
| Example 1 | 3.0 | 172% | 92% | 81% | 65% | 30% | 3.044 | 1.632 | 1.436 | 1.148 | 0.525 |
| Example 2 | 3.5 | 151% | 89% | 68% | 51% | 23% | 2.679 | 1.572 | 1.210 | 0.896 | 0.401 |
| Example 3 | 4.0 | 139% | 85% | 70% | 46% | 20% | 2.462 | 1.510 | 1.237 | 0.813 | 0.359 |
| Example 4 | 4.5 | 137% | 76% | 61% | 40% | 14% | 2.430 | 1.344 | 1.083 | 0.715 | 0.246 |
| Example 5 | 5.0 | 119% | 63% | 53% | 30% | 12% | 2.112 | 1.121 | 0.935 | 0.525 | 0.208 |
| Example 6 | 5.5 | 98% | 55% | 35% | 25% | 6% | 1.730 | 0.973 | 0.617 | 0.442 | 0.115 |
| Example 7 | 6.0 | 93% | 46% | 33% | 17% | 7% | 1.640 | 0.807 | 0.584 | 0.303 | 0.116 |

It will be understood that various modifications may be made to the embodiment disclosed herein. Therefore the above description should not be construed as limiting, but merely as exemplifications of preferred embodiments. For example, the suture can be predegraded before being placed into a suture retainer or package. As another example, a surgical article other than a suture can be predegraded in accordance with the methods described herein. Those skilled in the art will envision other modifications within the scope and spirit of the claims appended hereto.

What is claimed is:

1. A method comprising the steps of a) providing a surgical article made from a bioabsorbable material; b) subjecting the surgical article to an atmosphere of about 20% to about 70% relative humidity, at a temperature in the range of about 80° F. to about 200° F. for a period of time sufficient to predegrade the material; and c) coating the predegraded surgical article.

2. The method of claim 1 wherein the bioabsorbable material is a material selected from the group consisting of polymers of glycolide, lactide, caprolactone, trimethylene carbonate, dioxanone and physical and chemical combinations thereof.

3. The method of claim 1 wherein the bioabsorbable material comprises a copolymer of glycolide and lactide.

4. The method of claim 1 wherein the bioabsorbable material comprises a random copolymer derived from a major amount of glycolide and a minor amount of lactide.

5. The method of claim 4 wherein the random copolymer contains about 92 weight percent glycolide and about 8 weight percent lactide.

6. The method of claim 4 wherein step (b) comprises exposing the surgical article to a temperature of from about 125° F. to about 135° F.

7. The method of claim 1 wherein step (b) lasts for about 1 to about 12 days.

8. The method of claim 1 wherein step (b) comprises exposing the surgical article to an atmosphere of about 45% to about 55% relative humidity.

9. The method of claim 1 wherein step (b) lasts about 5 to about 8 days.

10. The method of claim 1 wherein the step of providing a surgical article comprises providing a suture.

11. The method of claim 10 wherein the suture is a braided suture.

12. The method of claim 10 wherein the suture is made from a random copolymer of glycolide and lactide.

13. The method of claim 12 wherein the suture is a braided multifilament suture.

14. The method of claim 13 wherein the suture is coated with a copolymer of ε-caprolactone and glycolide.

15. The method of claim 1 wherein the surgical article is sterilized prior to step (b).

16. The method of claim 1 further comprising the step of sterilizing the surgical article after step (b).

17. An article of manufacture comprising a moisture impervious package containing a suture including one or more filaments of a synthetic bioabsorbable polymer, the filaments having been exposed to an atmosphere of about 20% to about 70% relative humidity at a temperature in the range of about 80 to about 200° F. for at least one day and then coated prior to being packaged.

18. The article of claim 17 wherein the synthetic bioabsorbable polymer is selected from the group consisting of polymers of glycolide, lactide, caprolactone, trimethylene carbonate, dioxanone and physical and chemical combinations thereof.

19. The article of claim 17 wherein the synthetic bioabsorbable polymer comprises a random copolymer of glycolide and lactide.

20. The article of claim 17 wherein the one or more filaments are exposed to an atmosphere of about 45% to about 55% relative humidity at a temperature of from about 125° F. to about 135° F. prior to being packaged.

21. A method of suturing a wound comprising the steps of: a) providing a needled suture, the suture including one or more coated filaments of a synthetic bioabsorbable polymer, the filaments having been exposed prior to being coated to an atmosphere of about 20% to about 70% relative humidity, at a temperature in the range of about 80° F. to about 200° F. for a period of time sufficient to predegrade the needled suture; and b) passing the predegraded needled suture through tissue surrounding the wound to create wound closure.

22. The method of claim 21 wherein the suture possesses about 50% of its original strength at day 5 following step (b).

23. The method of claim 21 wherein the suture possesses about 0% of its original strength after about 10 to about 14 days following step (b).

* * * * *